(12) United States Patent
Guzman

(10) Patent No.: US 6,406,604 B1
(45) Date of Patent: Jun. 18, 2002

(54) MULTI-DIMENSIONAL ELECTROPHORESIS APPARATUS

(76) Inventor: Norberto A. Guzman, P.O. Box 6006, East Brunswick, NJ (US) 08816

( * ) Notice: Subject to any disclaimer, the term of this patent is extended or adjusted under 35 U.S.C. 154(b) by 0 days.

(21) Appl. No.: 09/436,186

(22) Filed: Nov. 8, 1999

(51) Int. Cl.[7] .............................................. G02N 27/26
(52) U.S. Cl. ....................... 204/601; 204/604; 204/605
(58) Field of Search ................................ 204/601, 604, 204/605

(56) References Cited

U.S. PATENT DOCUMENTS 5,944,971 A * 8/1999 Foote ......................... 204/456
RE36,350 E * 10/1999 Swedberg et al. ........ 210/198.2

FOREIGN PATENT DOCUMENTS

WO          WO9510344     *  4/1995

OTHER PUBLICATIONS

Petersson et al. ("Miniaturised on–line solid–phase extraction for enhancement of concentration sensitivty in capillary electrophoresis", Journal of Chromatography A, 841 (1999) 249–261).*

* cited by examiner

Primary Examiner—Jill Warden
Assistant Examiner—Alex Noguerola
(74) Attorney, Agent, or Firm—Squire, Sanders & Dempsey L.L.P.

(57) ABSTRACT

An electrophoresis apparatus is generally disclosed for sequentially analyzing a single sample or multiple samples having one or more analytes in high or low concentrations. The apparatus comprises a relatively large-bore transport capillary which intersects with a plurality of small-bore separation capillaries. Analyte concentrators, having antibody-specific (or related affinity) chemistries, are stationed at the respective inter-sections of the transport capillary and separation capillaries to bind one or more analytes of interest. The apparatus allows the performance of two or more dimensions for the optimal separation of analytes.

28 Claims, 8 Drawing Sheets

MULTI-DIMENSIONAL ELECTROPHORESIS APPARATUS

FIELD OF THE INVENTION

The present invention relates generally to the analysis of chemical and biological materials and, more particularly, to an improved electrophoresis apparatus which simultaneously performs multiple analyses on a plurality of analytes.

BACKGROUND OF THE INVENTION

Electrophoresis is a known technique for separating and characterizing constituent chemical and/or biological molecules, or analytes, present in simple and complex matrices undergoing analysis. Candidate sample compounds include drugs, proteins, nucleic acids, peptides, metabolites, biopolymers and other substances which exist in simple and complex forms.

Conventional systems are based on interchangeable cartridges which house a thin capillary tube equipped with an optical viewing window that cooperates with a detector. Sample solutions and other necessary fluids are placed in vials (cups) positioned beneath inlet and outlet ends of the capillary tube by means of a rotatable table.

When high voltage is applied to a capillary filled with an appropriate solution and/or matrix, molecular components migrate through the tube at different rates and physically separate. The direction of migration is biased toward an electrode with a charge opposite to that of the molecules under investigation. As the molecules pass the viewing window, they are monitored by a UV or other detector which transmits an absorbance or appropriate signal to a recorder. The absorbance or appropriate values are plotted as peaks which supply analytical information in the form of electropherograms.

Electrophoresis separation relies on the different migration of charged particles in an electric field. Migration speed is primarily influenced by the charge on a particle which, in turn, is determined by the pH of the buffer medium. Electric field strength and molecular size and shape of the analyte also influence migration behavior.

Electrophoresis is a family of related techniques that perform high efficiency separations of large and small molecules. As one embodiment of this science, capillary electrophoresis is effective for obtaining rapid and high separations in excess of one-hundred-thousand plates/meter. Because it is a non-destructive technique, capillary electrophoresis preserves scarce physical samples and reduces consumption of reagents. A fused silica (quartz) capillary, with an inner bore diameter ranging from about 5 microns to about 200 microns and a length ranging from about 10 centimeters to about 100 centimeters, is filled with an electrically conductive fluid, or background electrolyte, which is most often a buffer. Since the column volume is only about 0.5 to about 30 microliters, the sample introduction volume is usually measured in nanoliters, picoliters and femtoliters (ideally 2% of the total volume of the column). As a consequence, the mass sensitivity of the technique is quite high.

Improved instrumentation and buffer-specific chemistries now yield accurate peak migrations and precise area counts for separated analytes. But, capillary electrophoresis is still limited by concentration sensitivity.

To overcome this deficiency, a series of solid-phase micro-extraction devices have been developed for selective and non-selective molecular consolidation. These devices, which are used on-line with a capillary tube, are commonly known as analyte concentrators containing affinity probes to bind target compounds. Typical embodiments are described in U.S. Pat. No. 5,202,010 which is incorporated by reference in this disclosure. Other relevant teachings are provided by U.S. Pat. No. 5,741,639 which discloses the use of molecular recognition elements; and U.S. Pat. No. 5,800,692 which discloses the use of a pre-separation membrane for concentrating a sample.

Even with the advent of analyte concentrators, there is still a need to improve the sensitivity levels for samples that exist in sub-nanomolar quantities. This deficit is particularly acute in the clinical environment where early detection of a single molecule may be essential for the identification of a life-threatening disease.

Known capillary electrophoresis instruments are also limited by low-throughput, i.e., the number of samples that can be analyzed in a specified period of time. U.S. Pat. No. 5,045,172, which is incorporated by reference, describes an automated, capillary-based system with increased analytical speed. The '172 patent represents a significant improvement over the prior art. But, throughput is still relatively low because the instrument uses only one capillary which performs single sample analyses in approximately 30 minutes.

U.S. Pat. No. 5,413,686 recognizes the need for a multifunctional analyzer using an array of capillary tubes. Like other disclosures of similar import, the '686 patent focuses on samples having relatively high concentrations. There is no appreciation of the loadability and sensitivity necessary for analyzing diluted samples, or samples present at low concentrations in a variety of liquids or fluids.

Based on these deficiencies, there exists an art-recognized need for an electrophoresis instrument having higher loadability, better detectability of constituent analytes, faster throughput and multi-functional capability for analyzing a plurality of components in a single sample and/or a plurality of samples with high and low concentrations using a variety of chromophores, detectors and/or pre-concentration devices.

OBJECTS OF THE INVENTION

Accordingly, it is a general object of the present invention to provide an improved electrophoresis apparatus having at least one transport capillary, at least one separation capillary and an analyte concentrator positioned therebetween.

It is another object of the present invention to provide an electrophoresis apparatus having greater operating efficiency, detectability and throughput.

An additional object of the present invention is to provide a user-friendly, sample preparation step which is designed to eliminate unwanted analytes that occupy binding sites and contaminate the inner walls of capillaries or channels.

A further object of the present invention is to provide an electrophoresis apparatus that can analyze multiple samples having a single constituent, or multiple constituents of a single sample.

It is a further object of the present invention to provide an electrophoresis apparatus which uses more than one analyte concentrator to sequentially bind more than one analyte in a single complex matrix, or in multiple matrices of simple or complex configuration.

It is yet another object of the present invention to provide an electrophoresis apparatus having enhanced loadability and sensitivity which is capable of analyzing samples present in a wide range of concentrations, including those found at low concentrations in diluted liquids or fluids with simple or complex matrices.

It is a further object of the present invention to provide an electrophoresis apparatus that delivers high-throughput for screening and analyzing a wide variety of samples in multiple application areas, utilizing a single or multiple dimension separation principle or mode.

Another object of the present invention is to provide an electrophoresis apparatus which uses more than one separation method to sequentially permit binding to, and elution from, an analyte concentrator to effect the separation of one or more analytes.

It is another object of the present invention to provide an automated, miniaturized desk-top electrophoresis apparatus for bioanalysis and other applications.

Additional objects of the present invention will be apparent to those skilled in the relevant art.

SUMMARY OF THE INVENTION

In one aspect of the invention, a sample including a number of analytes of interest is passed through a relatively large-bore transport capillary orthogonal to a plurality of smaller-bore separation capillaries. An analyte concentrator is positioned at each intersection of the transport capillary and separation capillaries.

After the sample has been passed through each of the analyte concentrators, and after the analytes of importance are captured by each concentrator matrix, a selected buffer is applied to each analyte concentrator to free the system of salts and other nonrelevant components. For example, a typical buffered solution is sodium tetraborate having a pH in the range of 7.0 to 9.0. The bound analytes are then eluted from each concentrator matrix in a sequentially time-controlled fashion using an aliquot or plug of an optimal eluting solution. The process continues until each of the analytes has been removed from the concentrator matrices and passed through the detector by high resolution electrophoresis migration. To increase the sensitivity of the analytes, an additional analyte concentrator containing a chromophoric reagent may be placed in one or more of the separation capillaries to react with the analyte present in that capillary. Alternatively, the eluting solution may contain a chromophoric reagent allowing decoupling and derivatization to occur simultaneously. The derivatized analytes can then be isolated in the separation capillary.

To separate and analyze multiple samples with the electrophoresis apparatus of the invention, individual separation capillaries are provided, each of which contains an analyte concentrator that enriches the analytes present in diluted solutions of low concentration. Multiple elutions are carried out in a manner similar to that performed when analyzing a single sample. Effective results can also be achieved using solutions that contain an appropriate eluting chemical and a chromophoric reagent to simultaneously elute the targeted analyte and enhance sensitivity. As with a single-sample analyzer, an extra analyte concentrator may be placed in one or more of the separation capillaries to allow on-line derivatization of analytes to achieve even further enhancement of concentration sensitivity. In addition, an extra analyte concentrator may be placed in one or more of the separation capillaries to permit biochemical reactions, such as the on-line cleavage of proteins to generate peptides.

An analyte concentrator may also be used to quantify enzymatic products generated by the action of one or more pharmacological agents during a specific enzyme reaction. Furthermore, the use of an analyte concentrator coupled to a different mode of electrophoresis can be used to differentiate structurally related substances present in biological fluids or tissue specimens. For example, the identification and characterization of natural proteins from artificially-made proteins or other chemicals in serum.

All reactions described above can be performed in an apparatus containing a format that includes either capillaries or channels. In addition, the migration of analytes can be accomplished by an electrical or mechanical pump.

DETAILED DESCRIPTION OF THE INVENTION

Figure 1:
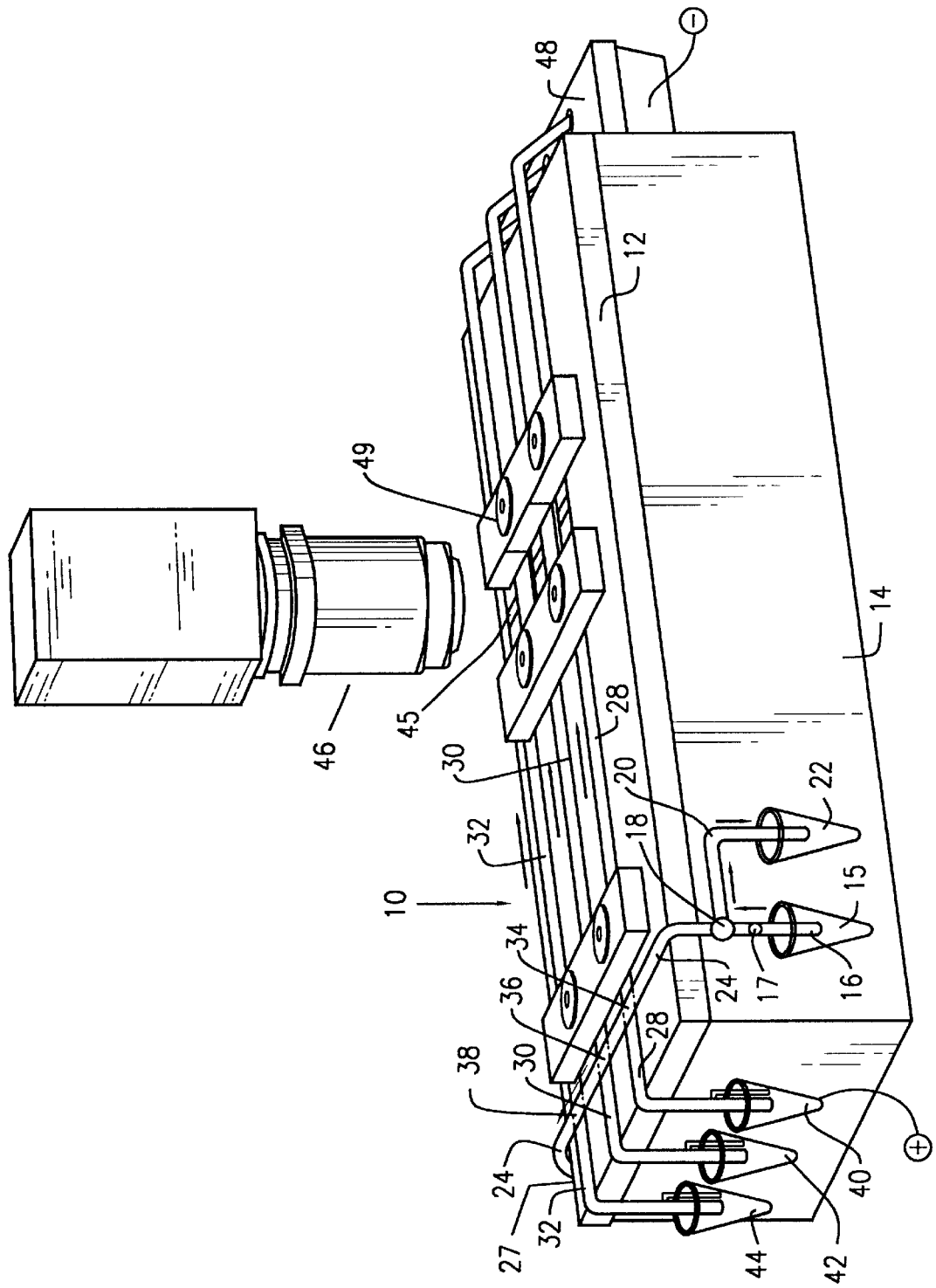
FIG. 1 is a perspective view of the electrophoresis apparatus of the present invention.

FIG. 1 illustrates electrophoresis apparatus 10 of the present invention. In its elementary mode (e.g., FIG. 8), apparatus 10 performs single sample studies on chemical or biological matrices having constituents or analytes of interest. But, according to the operating principles shown and described, apparatus 10 can perform multiple analyses by detecting and measuring the presence of a plurality of analytes (for example, three). Suitable and representative analytes may include narcotics, glucose, cholesterol or pharmaceutical drugs that may be present in urine or whole blood, as well as small and large molecular weight substances having simple and complex structures.

As shown in FIG. 1, apparatus 10 includes platform 12 having side wall 14. Sample cup 15 is mounted laterally on side wall 14. A large-bore (150–300 mm in length× 500–2000 μm I.D.), non-selective introduction capillary 16 and large-volume (1–3 ml) analyte concentrator 17 connect sample cup 15 to a first input of valve 18 which is coupled, by capillary 20, to waste container 22 positioned on side wall 14 adjacent to sample cup 15. In a typical configuration, analyte concentrator 17 comprises a matrix-like assembly of the type shown in U.S. Pat. No. 5,202,010. The collective mass of the matrix is provided by large quantities of microstructures such as beads, platelets, chips, fibers, filament or the like. Individual substrates can be made from glass, plastic, ceramic or metallic compositions, and mixtures thereof. Coated or otherwise deposited onto the microstructures are immobilized analyte-specific antibodies or other affinity chemistries which are suitable for characterizing and separating particular analytes of interest. Representative antibodies include those which act against peptide hormones such as insulin, human growth hormone and erythropoietin. These antibodies are readily available from commercial vendors such as Sigma-Aldrich Co., St. Louis, Mo. and Peninsula Laboratories, Belmont, Calif.

The present invention contemplates a user-friendly, sample preparation step which is designed to eliminate unwanted analytes that occupy binding sites and contaminate the inner walls of capillaries or channels. This procedure will now be described with specific reference to apparatus 10 of FIG. 2.

A first output of valve 18 is placed in the closed position and a quantity of solution from sample cup 15 is introduced into analyte concentrator 17. Depending on its pre-selected matrix, analyte concentrator 17 traps, in a non-specific manner, many (up to 100 or more) different analytes, including the analytes under investigation. Sample cup 15 is then replaced by a buffer container (not shown). This replacement step may be accomplished by a rotatable table mechanism of the type described in U.S. Pat. No. 5,045,172. Thereafter, a quantity of buffer is injected through analyte concentrator 17 to remove excess amounts of sample and unwanted sample components. Because valve 18 remains closed during this operation, excess and unwanted samples are passed into waste container 22.

Figure 2:
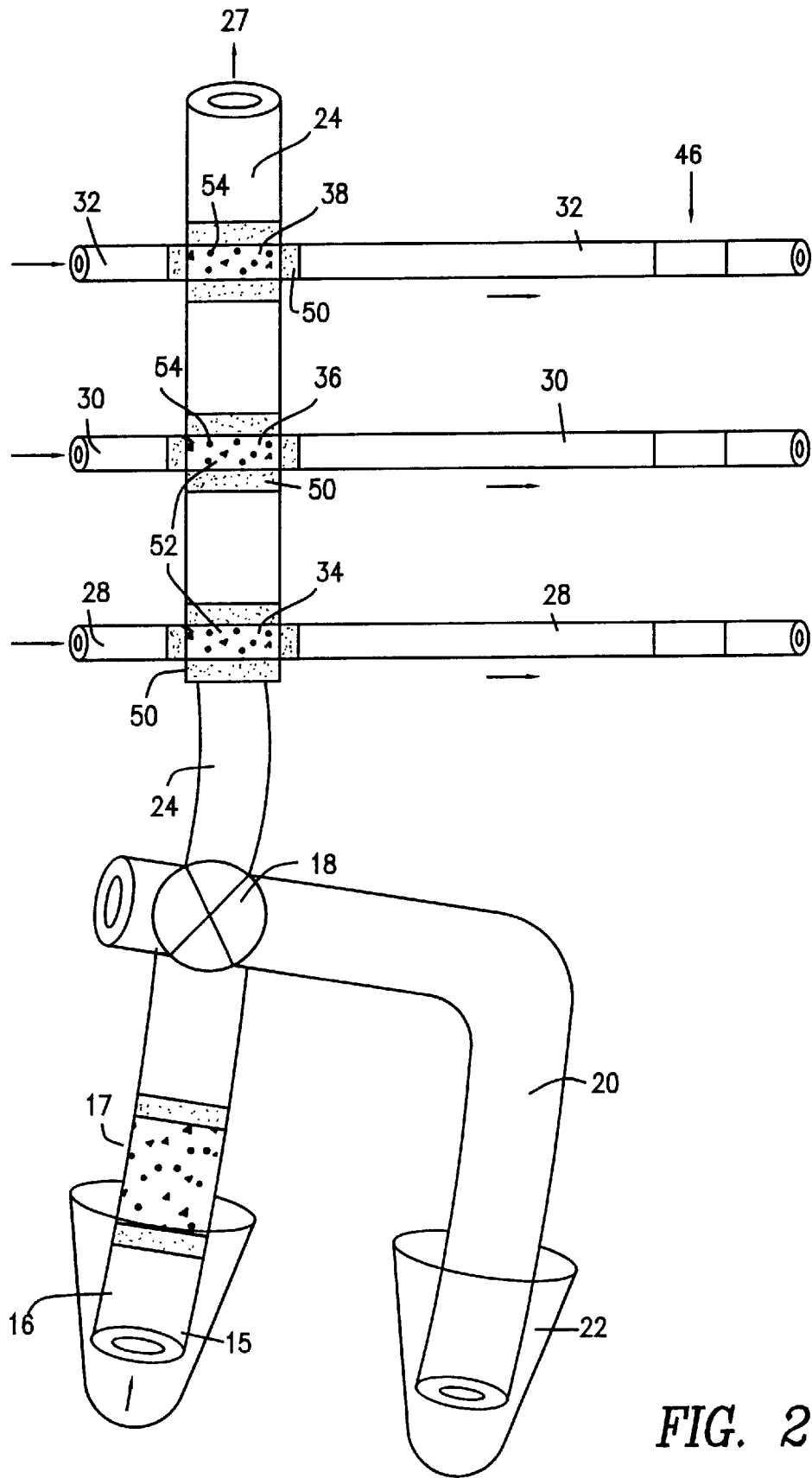
FIG. 2 is an enlarged, elevated view of a plurality of analyte concentrators stationed at the respective intersections of a large bore transport capillary and an equal plurality of small bore separation capillaries.

The remainder of apparatus 10 can now be considered. A second output of valve 18 communicates with transport capillary 24 which, as shown by FIG. 2, intersects a plurality, here shown as three, of narrow-bore (20–75 $\mu$m) separation capillaries 28, 30 and 32. Analyte concentrators 34, 36 and 38 are sequentially stationed at the intersections of transport capillary 24 and separation capillaries 28, 30 and 32 to trap or bind different analytes of interest.

Figure 3:
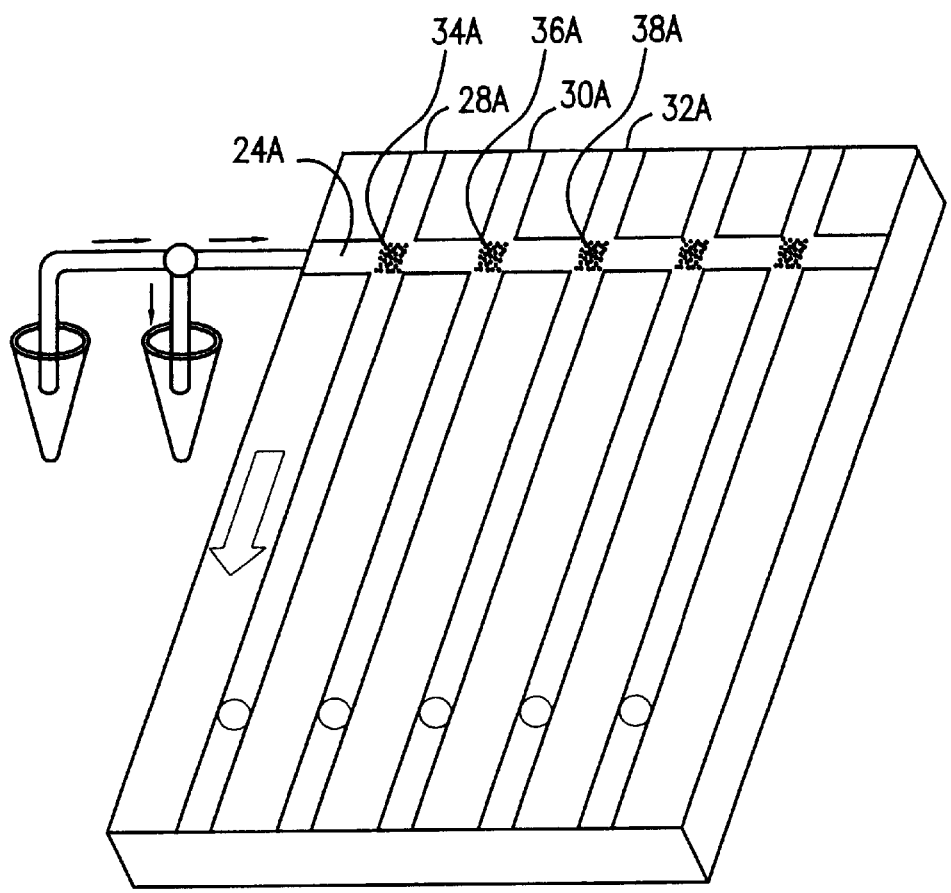
FIG. 3 is an elevated view of a second embodiment of the present invention, showing a plurality of analyte concentrators stationed at the respective intersections of an alternative transport channel and an equal plurality of separation channels.
Figure 3A:
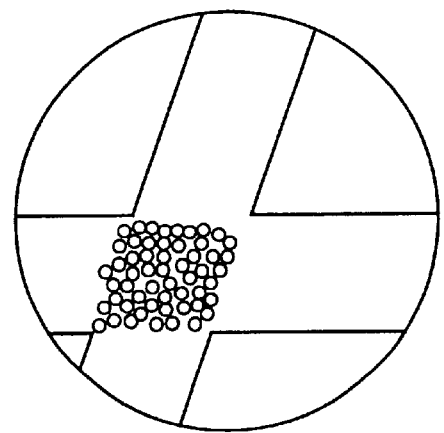
FIG. 3A is an enlarged view of the described intersection containing the analyte concentrator microstructure.

A first end (the left as viewed in FIG. 1) of separation capillary 28 is initially placed in buffer solution cup 40. In like manner, a first end of separation capillary 30 is placed in buffer solution cup 42; and a first end of separation capillary 32 is placed in buffer solution cup 44. A major portion of separation capillaries 28, 30 and 32 extend in parallel over the upper surface of platform 12 through detection zone 45 where the analytes respectively present in each of the separation capillaries are identified by an otherwise conventional detector 46. Separation capillaries 28, 30 and 32, which terminate at ground connection 48, may be secured to the upper surface of platform 12 by holders 49. Platform 12 can also take the form of an interchangeable cartridge with pre-positioned capillaries and analyte concentrators properly secured and aligned with respect to the optical system. In yet another embodiment, best shown in FIG. 3, transport channel 24A and separation channels 28A, 30A and 32A, having uniform and concave shapes, can be engraved, etched or otherwise formed into a glass or plastic microchip using known lithography or other manufacturing techniques. Analyte concentrators 34A, 36A and 38A are disposed at the respective intersections of transport channel 24A and separation channels 28A, 30A and 32A as previously described.

When the sample preparation step is complete, valve 18 is opened to the main system and a buffer (e.g., sodium tetraborate) is passed through introduction capillary 16 and analyte concentrator 17. At this time, the analytes of interest are released from analyte concentrator 17 using an eluting solution, along with other analyte constituents present in the sample. The analytes of interest and all the other analytes captured and released by concentrator 17 are passed through transport capillary 24 to analyte concentrators 34, 36 and 38 which, as described below with reference to FIG. 3, contain a large quantity of microstructures that are capable of binding different analytes of interest; that is, each of the analyte concentrators 34, 36 and 38 select and isolate a different one of the analytes under investigation. Excess amounts of sample then pass through the other end of transport capillary 24 to waste container 27. Transport capillary 24 is subsequently washed with running buffer until unwanted substances are removed.

Separation capillaries 28, 30 and 32 are filled hydrodynamically (pressure or vacuum) with an appropriate electrophoresis separation buffer which occupies the entire volume of the capillary or channel. Immobilized analytes on a solid support are stable for long periods of time. As a result, large numbers of analytes can be sequentially separated over time, thereby providing high throughput for the apparatus of the present invention. Separation capillary 28 is first activated by introducing a plug of an appropriate eluting buffer from cup 40 by hydrodynamic (pressure or vacuum) or electrokinetic methods to desorb or elute analytes bound to analyte concentrator 34. The eluting buffer is immediately followed by a freshly prepared electrophoresis separation buffer present in replacement cup 40. Then, the power supply connected to cup 40 is activated to begin the process of analyte separation.

As shown in Table 1, with insulin taken as representative, a typical analysis involves the targeted analyte of interest, its corresponding antibody, an appropriate buffer and eluting solution.

TABLE 1

| Antigen | Antibody | Sep. Buffer+ | Eluting Solution* |
| --- | --- | --- | --- |
| Insulin | Anti-insulin antibody | Sodium tetraborate (pH 8.5) | Magnesium Chloride or Ethylene Glycol |

+Concentrations of electrophoresis separation buffer may range from 50 mM to 200 mM.
*Elution of other antigens or haptens may require a different eluting method. Effective eluting buffers include a 2 M solution of Magnesium Chloride and a 25% solution of Ethylene Glycol.

When the initial separation is complete, the next cycle, using separation capillary 30 and analyte concentrator 36, is performed in a similar manner, i.e., the analyte is eluted from concentrator 36 and then separated by eletrophoresis migration in separation capillary 30. During these operations, the power supply is connected to one analyte concentrator-separation capillary system at a time.

Separated analytes are then passed sequentially to detection zone 45 where each analyte is recognized and measured by detector 46 using, for example, known UV or fluorescence techniques. In one embodiment of the present invention, a single, bi-directional detector is indexed laterally above platform 12 to detect analytes of interest in separation capillaries 28, 30 and 32 or separation channels 28A, 30A and 32A. Other sub-assemblies could include a single, fixed detector and movable platform 12 which operates to position separation capillaries 28, 30 and 32 or separation channels 28A, 30A and 32A beneath the detector. Multiple detectors and movable platforms configured for X, Y and Z indexing are also contemplated.

Figure 4:
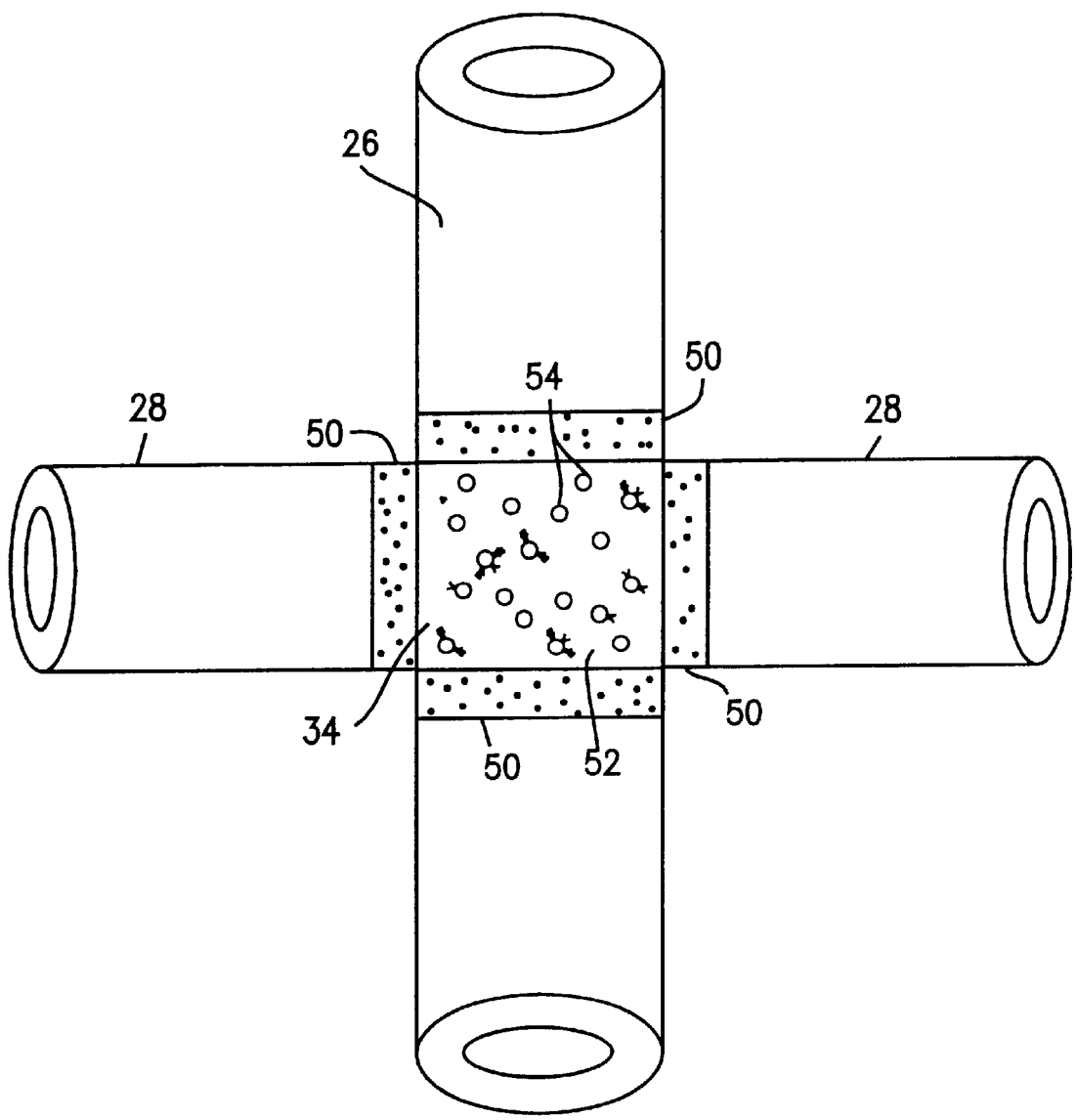
FIG. 4 is an enlarged, elevated view of an analyte concentrator stationed at the intersection of a transport capillary and a separation capillary.

FIG. 4 illustrates the location of analyte concentrator 34 stationed at the intersection of transport capillary 24 and separation capillary 28. As shown in FIG. 4, and in U.S. Pat. No. 5,203,010, porous end plates or frits 50, which permit fluid flow, are provided in transport capillary 24 and separation capillary 28 to act as barriers for holding microstructures 54 in analyte concentrator 34.

Figure 5:
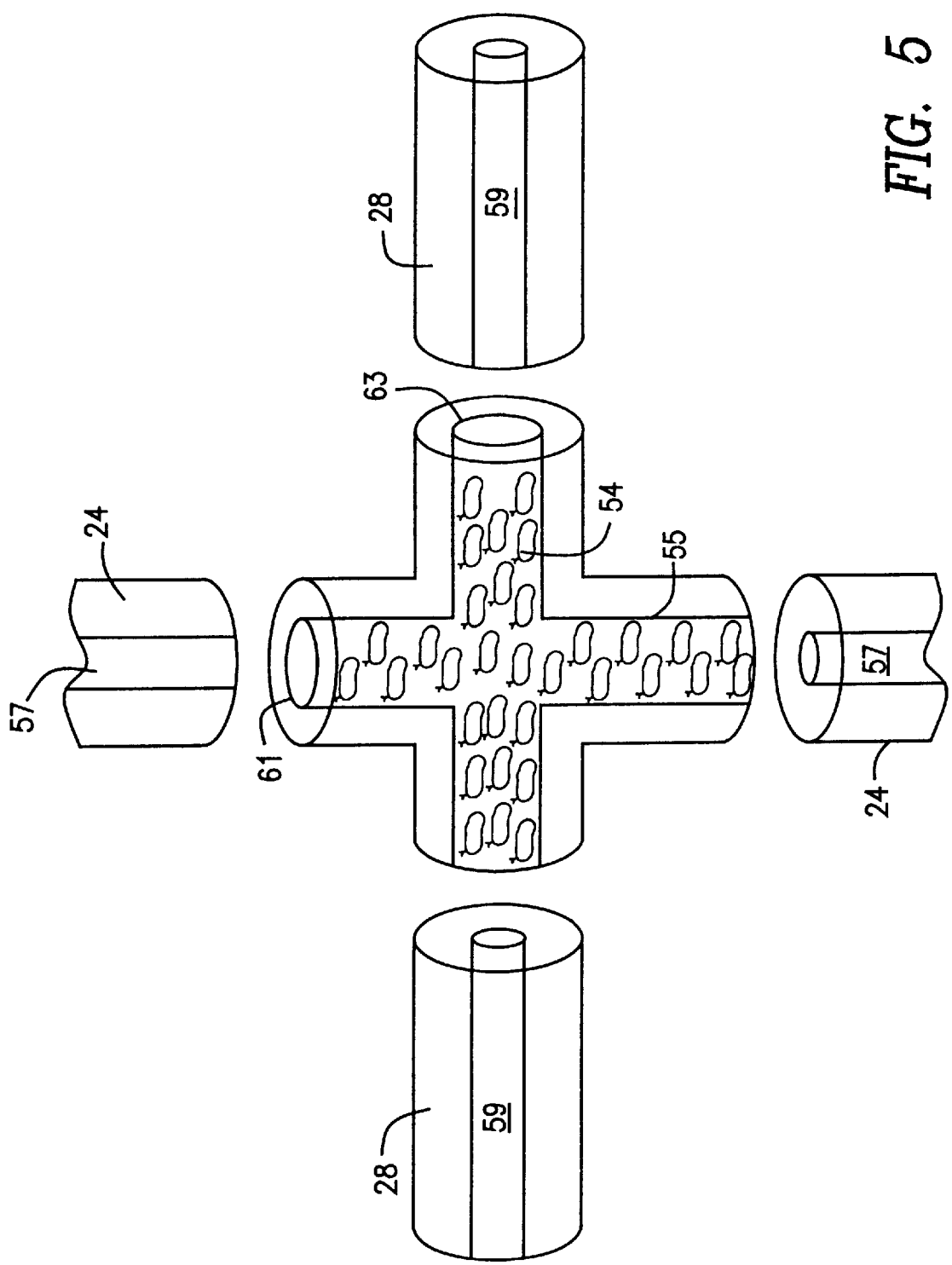
FIG. 5 is an elevated view of an analyte concentrator in the form of a cross-shaped capillary.

Alternatively, as shown in FIG. 5, analyte concentrator 55 can be fabricated by using two constricted areas with no frits at all. Analyte concentrator 55, in the form of a cross-shaped capillary, has inner diameter 61 and 63 pre-formed in relation to inner diameter 57 of transport capillary 24 and inner diameter 59 of separation capillary 28.

Analyte concentrator capillary 55 contains a plurality of previously described microstructures 54 which are larger than inner diameters 57 and 59. They are typically coated with non-specific chemistries such as C-18 or highly specific antibodies or antigens having an affinity for one of the analytes under investigation. Several other well-known chemistries can also be used.

In the embodiment illustrated by FIG. 5, microstructures 54 are retained or confined in the interior of analyte concentrator 55 by making inner diameter 57 of transport capillary 24 smaller than inner diameter 61 of analyte concentrator 55. In like manner, inner diameter 59 of separation capillary 28 is smaller than inner diameter 63 of analyte concentrator 55. For example, inner diameters 57 and 59 may be one-quarter to one-half the size of inner diameters 61 and 63.

To increase detection sensitivity for a particular analyte, a chromophore may be added to the eluting buffer to elute and tag the bound analyte for the purpose of enhancing the ultraviolet absorptivity, fluorescence, phosphorescence, chemiluminescence or bioluminescence of the analyte as it passes through detector 46.

Figure 6:
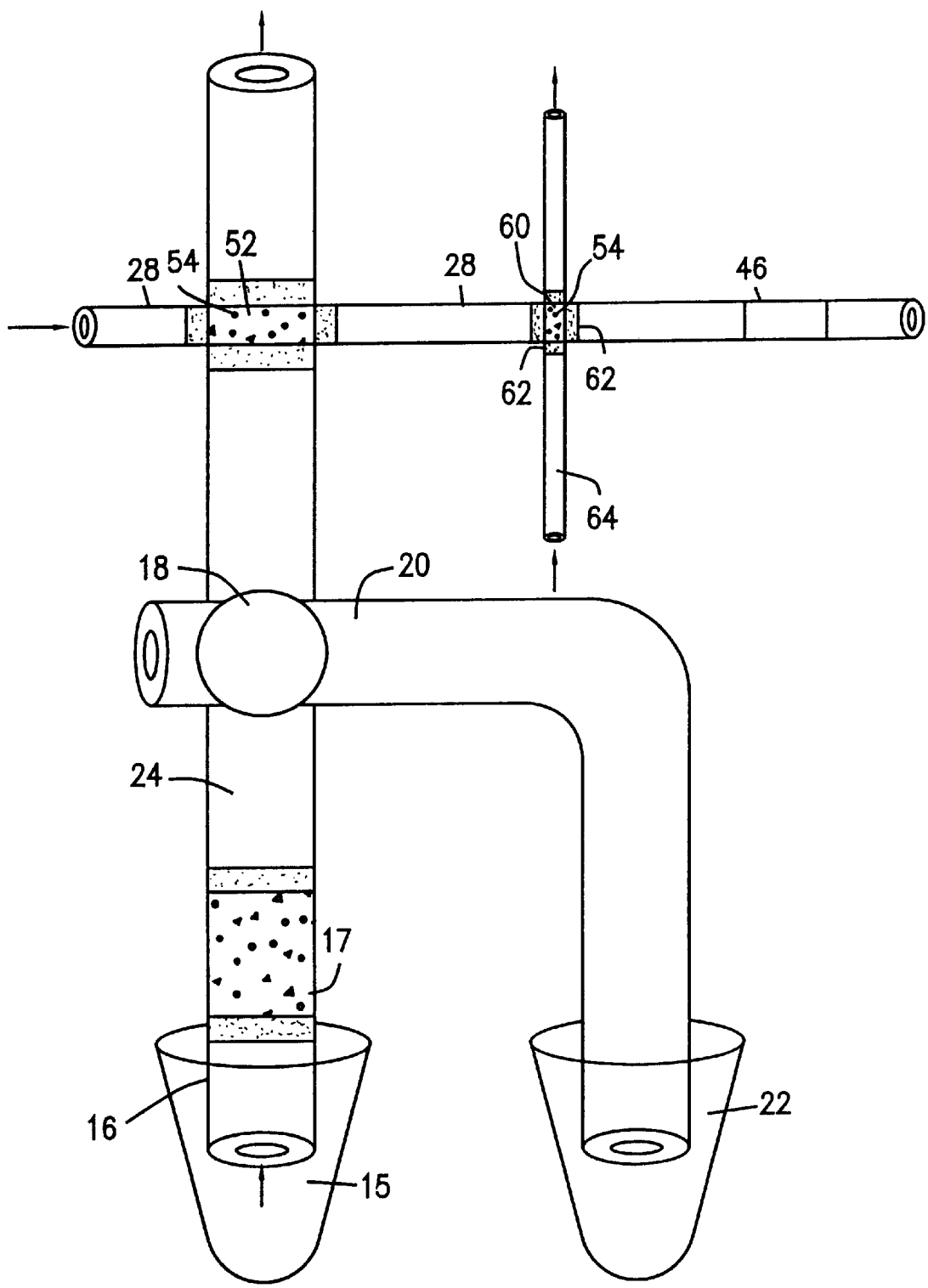
FIG. 6 is an elevated view of the electrophoresis apparatus of the present invention, showing an analyte concentrator disposed along the length of a separation capillary.

In an alternative technique to increase detection sensitivity, additional analyte concentrator 60 may be placed in one of separation capillaries 28, 30 and 32, as shown in FIG. 6. Analyte concentrator 60 has a plurality of microstructures 54 coated with a chromophoric agent or antibody that binds to a portion of a chromophoric agent which increases ultraviolet absorptivity, fluorescence or phosphorescence when bound to a minute quantity of a specific analyte. Frits 62 are located at the input and output of analyte concentrator 60, and narrow capillary 64, which intersects with separation capillary 28, carries a buffer to periodically cleanse microstructures 54 in analyte concentrator 60 after each analysis.

An analyte tagged with a chromophoric agent is more readily identified by the apparatus of the present invention, thereby increasing the sensitivity of analyte detection by as much as 100 times or more. Many different chromophoric agents emit light when they bind a specific functional group to form a product molecule in an electronically excited state.

Figure 7:
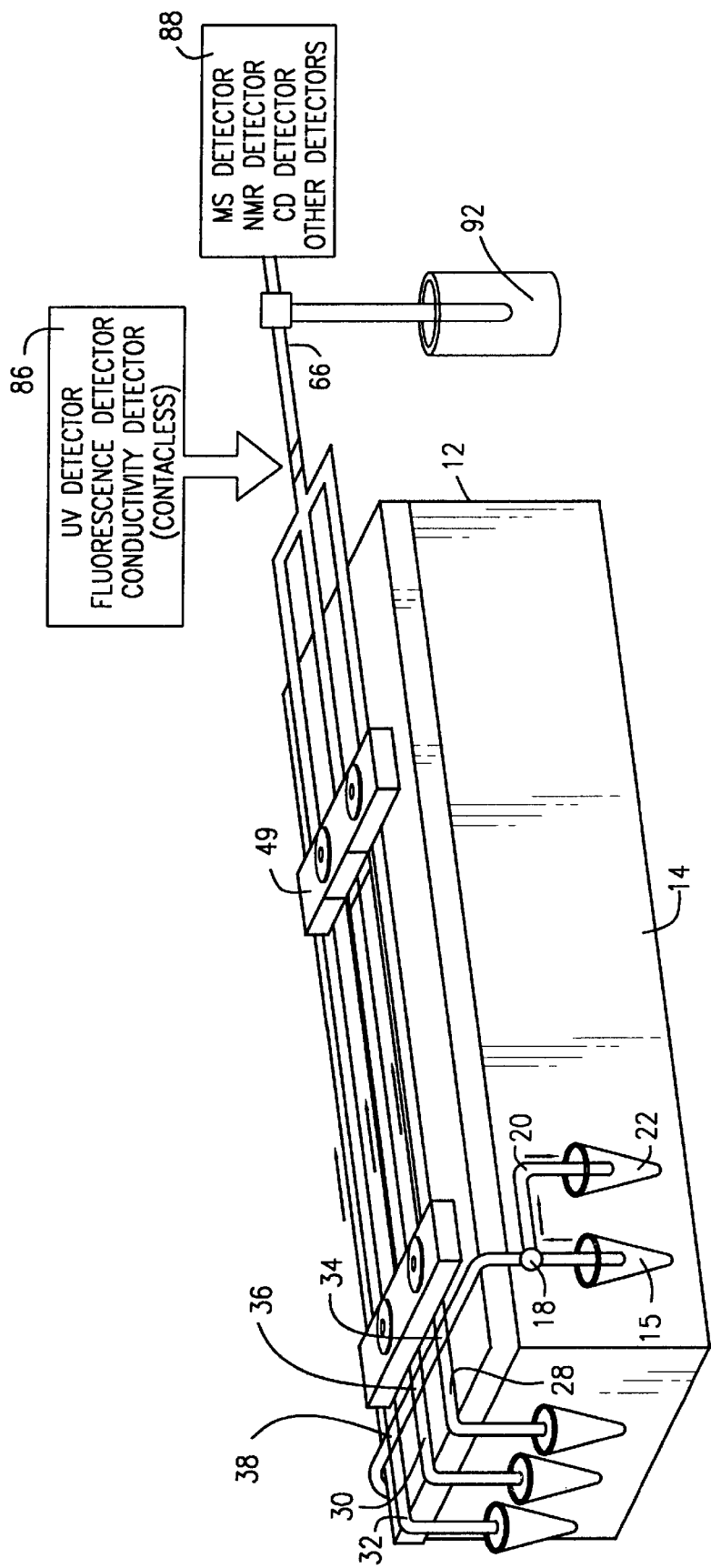
FIG. 7 is a perspective view of a third embodiment of the present invention, showing a plurality of separation capillaries connected to a single outlet capillary for sequential detection.

The alternative embodiment illustrated by FIG. 7 is similar to that shown in FIG. 1. But, the FIG. 7 embodiment is different because the output ends of separation capillaries 28, 30 and 32 are connected to each other at the interface with a single outlet capillary 66 which cooperates with on-column detector 86 that senses ultraviolet (UV) or fluorescent energy. The exit position of outlet capillary 66 may also be connected (as shown) to off-column detector 88 which comprises an electrochemical, mass spectrometry, circular dichroism detector or nuclear magnetic resonance detector.

The electrophoresis apparatus of FIG. 7 employs multiple separation capillaries or channels for sample concentration, but only one outlet capillary for sample detection. This coordinated separation by individual capillaries may be sequentially activated and controlled by well-known electronic circuitry. Like the FIG. 1 embodiment, preceding analytes are completely separated and detected before the next separation operation is activated.

Figure 8:
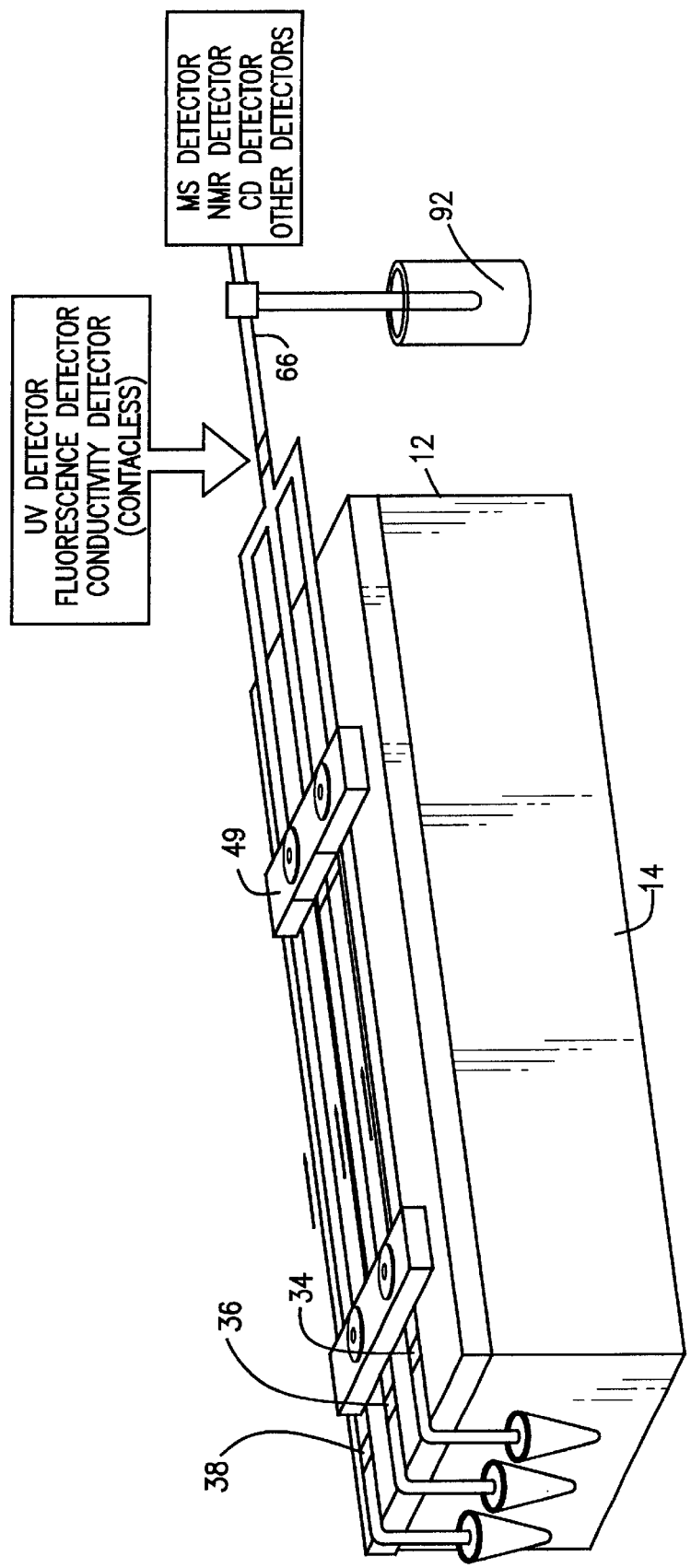
FIG. 8 is a perspective view of a fourth embodiment of the present invention, showing a plurality of separation capillaries adapted to analyze multiple samples according to the techniques described in this specification.

The electrophoresis apparatus of FIG. 8 is similar to that of FIG. 7, but it is adapted to work with multiple samples (here, e.g., three) having a simple or complex component. There is no introduction capillary 16 or sample cup 15 as provided by embodiments of FIG. 1 and FIG. 7. Separation capillaries 28, 30 and 32 are equipped with single analyte concentrators 34, 36 and 38, respectively. Individual samples are directly and sequentially delivered to separation capillaries 28, 30 and 32 and the analytes of interest are captured using suitable chemistries as previously described. The capillaries may be washed with buffer until all unwanted substances are removed. Like the FIG. 7 embodiment, separation capillaries 28, 30 and 32 are activated in series one after the other. When all the analytes are separated in a single capillary, the apparatus begins the next separation cycle. In each of the described embodiments, apparatus 10 provides greater efficiency and higher throughput when compared to prior art devices.

Various modifications and alterations to the present invention may be appreciated based on a review of this disclosure. These changes and additions are intended to be within the scope and spirit of this invention as defined by the following claims.

What is claimed is:

1. An electrophoresis apparatus comprising:
   an inlet opening for introducing a sample to be analyzed;
   a transport capillary extending in a longitudinal direction;
   at least one separation capillary disposed at a pre-selected angle relative to said transport capillary, wherein the transport capillary intersects and is in fluid communication with said at least one separation capillary;
   at least one analyte concentrator positioned adjacent to said transport capillary and said separation capillary;
   said analyte concentrator including a plurality of microstructures;
   said microstructures carrying at least one affinity element adapted to attract at least one analyte of interest from said sample which passes through said analyte concentrator; and
   a detector means for identifying and characterizing said analyte of interest,
   wherein said inlet opening is provided by an introduction capillary having first and second ends with a non-specific analyte concentrator disposed therebetween and said introduction capillary is connected to said transport capillary.

2. The electrophoresis apparatus of claim 1 wherein said separation capillary is perpendicular to said transport capillary.

3. The electrophoresis apparatus of claim 1 wherein said analyte concentrator is positioned at the intersection between said transport capillary and said separation capillary.

4. The electrophoresis apparatus of claim 1 wherein a plurality of separation capillaries are disposed at pre-selected angles relative to said transport capillary.

5. The electrophoresis apparatus of claim 4 wherein a plurality of analyte concentrators are positioned adjacent to said transport capillary and said plurality of separation capillaries.

6. The electrophoresis apparatus of claim 1 wherein a plurality of separation capillaries are perpendicular to said transport capillary.

7. The electrophoresis apparatus of claim 6 wherein a plurality of analyte concentrators are positioned at the intersection between said transport capillary and said plurality of separation capillaries.

8. The electrophoresis apparatus of claim 7 wherein said inlet opening is provided by an introduction capillary having first and second ends with a non-selective analyte concentrator disposed therebetween.

9. The electrophoresis apparatus of claim 8 wherein said introduction capillary is connected to said transport capillary by a valve.

10. The electrophoresis apparatus of claim 1 wherein said affinity element is an analyte-specific antibody.

11. The electrophoresis apparatus of claim 1 wherein said analyte concentrator has a matrix-like assembly provided by a plurality of microstructures taken from the group consisting of beads, platelets, chips, fibers and filaments.

12. The electrophoresis apparatus of claim 11 wherein said analyte concentrator is defined by porous end walls disposed in said transport capillary and said separation capillary.

13. The electrophoresis apparatus of claim 1 having an additional analyte concentrator disposed downstream in said separation capillary.

14. The electrophoresis apparatus of claim 13 wherein said additional analyte concentrator has a plurality of microstructures carrying a pre-selected chromophoric agent.

15. An electrophoresis apparatus comprising:
   an inlet opening for introducing a sample to be analyzed;
   a transport channel extending in a longitudinal direction;
   at least one separation channel disposed at a pre-selected angle relative to said transport channel, wherein the transport channel intersects and is in fluid communication with said at least one separation channel;
   said transport channel and said at least one separation channel being formed in a microchip;
   an analyte concentrator positioned adjacent to said transport channel and said separation channel;
   said analyte concentrator including a plurality of microstructures;
   said microstructures carrying at least one affinity element adapted to attract at least one analyte of interest from said sample which passes through said analyte concentrator; and
   a detector means for identifying and characterizing said analytes of interest, wherein said inlet opening is provided by an introduction channel having first and second ends with a non-specific analyte concentrator disposed therebetween and said introduction channel is connected to said transport channel.

16. The electrophoresis apparatus of claim 15 wherein said separation channel is perpendicular to said transport channel.

17. The electrophoresis apparatus of claim 15 wherein said analyte concentrator is positioned at the intersection between said transport channel and said separation channel.

18. The electrophoresis apparatus of claim 15 wherein a plurality of separation channels are disposed at pre-selected angles relative to said transport channel.

19. The electrophoresis apparatus of claim 18 wherein a plurality of analyte concentrators are positioned adjacent to said transport channel and said plurality of separation channels.

20. The electrophoresis apparatus of claim 15 wherein a plurality of separation channels are perpendicular to said transport channel.

21. The electrophoresis apparatus of claim 20 wherein a plurality of analyte concentrators are positioned at the intersection between said transport channel and said plurality of separation channels.

22. The electrophoresis apparatus of claim 21 wherein said inlet opening is provided by an introduction channel having first and second ends with a non-selective analyte concentrator disposed therebetween.

23. The electrophoresis apparatus of claim 22 wherein said introduction channel is connected to said transport channel by a valve.

24. The electrophoresis apparatus of claim 15 wherein said affinity element is an analyte-specific antibody.

25. The electrophoresis apparatus of claim 15 wherein said analyte concentrator has a matrix-like assembly provided by a plurality of microstructures taken from the group consisting of beads, platelets, chips, fibers and filaments.

26. The electrophoresis apparatus of claim 25 wherein said analyte concentrator is defined by porous end walls disposed in said transport channel and said separation channel.

27. The electrophoresis apparatus of claim 15 having an additional analyte concentrator disposed downstream in said separation channel.

28. The electrophoresis apparatus of claim 27 wherein said additional analyte concentrator has a plurality of microstructures carrying a pre-selected chromophoric agent.

* * * * *